United States Patent [19]
Ganguly et al.

[11] Patent Number: 4,926,871
[45] Date of Patent: May 22, 1990

[54] APPARATUS AND METHOD FOR NON-INVASIVELY AND AUTOMATICALLY MEASURING THE VOLUME OF URINE IN A HUMAN BLADDER

[75] Inventors: Dipankar Ganguly, Redmond; David Giuliani, Mercer Island, both of Wash.

[73] Assignee: International Biomedics, Inc., Bothell, Wash.

[21] Appl. No.: 226,148

[22] Filed: Jul. 28, 1988

Related U.S. Application Data

[63] Continuation of Ser. No. 5,152, Sep. 30, 1987, abandoned, which is a continuation-in-part of Ser. No. 732,344, May 8, 1985, abandoned.

[51] Int. Cl.$^5$ .................................................. A61B 8/00
[52] U.S. Cl. ........................... 128/660.07; 128/661.03
[58] Field of Search ...................... 128/660.01, 660.02, 128/661.02, 661.03, 660.07; 73/598, 602, 609, 612, 615, 861, 149; 382/6

[56] References Cited

U.S. PATENT DOCUMENTS

| | | | |
|---|---|---|---|
| 4,483,345 | 11/1984 | Miwa | 128/660.02 |
| 4,807,633 | 2/1989 | Fry | 128/660.02 |
| 4,852,578 | 8/1989 | Companion et al. | 128/661.03 |

*Primary Examiner*—Ruth S. Smith
*Attorney, Agent, or Firm*—Graybeal, Jensen & Puntigam

[57] ABSTRACT

An apparatus/method for measuring the volume of urine in a human bladder, including a scanhead and transceiver for transmitting a plurality of ultrasound signals (10, 24) into the bladder and for receiving the returning ultrasound signals (10,24). The apparatus further includes a signal processor for automatically processing the received signals (26), a digitizer for converting the analog signal into a series of digital data elements (28) and a CPU and signal processing software for processing the data elements (12,34) so as to determine the distance between the front and rear of the bladder or the area of the plane of the ultrasound signals, and for computing the volume of the bladder and hence the volume of urine in the bladder from the distance or area information (12, 34).

8 Claims, 5 Drawing Sheets

APPARATUS AND METHOD FOR NON-INVASIVELY AND AUTOMATICALLY MEASURING THE VOLUME OF URINE IN A HUMAN BLADDER

This is a continuation of application Ser. No. 005,152 filed on Jan. 20, 1987, (now abandoned) which in turn is a continuation-in-part of application Ser. No. 732,344 filed May 8, 1985 in the names of Dipankar Ganguly and David Giuliani (now abandoned).

DESCRIPTION

1. Technical Field

This invention generally concerns non-invasive ultrasonic medical apparatus, and more specifically concerns such an apparatus which is used to automatically determine the volume of urine in the bladder.

2. Background of the Invention

It is well known that bladder dysfunction is associated with a number of clinical conditions requiring treatment. It has been estimated that as many as twelve million urinary conditions requiring treatment occur each year in the United States. In many of these cases, it is important that the volume of urine in the bladder be accurately determined, sometimes on a frequent, if not substantially continuous, basis. This is especially true in cases involving spinal cord injuries which require bladder retraining and in those cases, such as post-operative recovery, where there is a temporary loss of bladder sensation and/or a loss of the normal voiding mechanism. Knowing the volume of urine in the bladder in such situations helps both bladder management and aids in the prevention of bladder over-distension.

The most common and reliable current technique of bladder volume determination is catheterization. Catheterization is used both as a diagnostic tool, and to actually empty the bladder when necessary. Typically, catheterization with respect to bladder volume is accurate to within approximately ten percent, and is currently the standard against which other methods are judged.

However, it is well known that there are significant disadvantages to catheterization. It is invasive and cannot be used for continuous monitoring, and further, it is uncomfortable for the patient. Still further, it is estimated that a significant number of people are seriously affected each year in the United States as a result of infection stemming from catheterization. The risk of infection alone is significant enough to provide a high incentive for a reasonable alternative.

Non-invasive procedures for bladder volume estimation are known, but are either unreliable or expensive or have some other significant disadvantage. Palpation and ascultatory percussion are known to be unreliable, while radiography and dye-excretion techniques are known to be similarly inaccurate and are now regarded to be obsolete at this point. Radio-isotopic procedures have also been used, and while accurate, are complicated and relatively expensive, as well as not being suitable for routine and/or continuous measurement.

Up to this point the most promising non-invasive technique has been conventional ultrasound-based measurement, where the output of the ultrasound apparatus is a two dimensional image of the bladder, from which actual measurements can be made and the volume calculated. However, the equipment for producing this ultrasound image is quite expensive and cumbersome to use. Further, the technique is not automatic and requires a trained operator. Hence, such methods have remained within the research arena and are not widely used.

Therefore, in summary, the non-invasive alternatives to catheterization all have significant disadvantages, so that catheterization remains the most commonly used procedure for determining bladder volume. As outlined above, however, it is invasive, traumatic to the patient, and is accompanied by a risk of infection.

DISCLOSURE OF THE INVENTION

Accordingly, the present invention is an apparatus for automatically measuring the volume of urine in a human bladder, including means for transmitting an ultrasound signal into the bladder, means for receiving the returning ultrasound signal, means for determining from the received signal information concerning a selected geometric characteristic of the bladder and means for automatically determining the volume of the bladder from said selected geometric characteristic.

Further, the invention includes a method for measuring the volume of urine in a human bladder, including the steps of transmitting an ultrasound signal into the bladder, receiving the returning ultrasound signal, determining from the received signal information concerning a selected geometric characteristic of the bladder, such as the diameter of the bladder, and then automatically determining the volume of the bladder from said selected geometric characteristic.

BEST MODE FOR CARRYING OUT THE INVENTION

Although the present invention uses ultrasound to determine bladder volume, it is unlike a traditional ultrasound apparatus which produces a two dimensional visual image of a target or portion of a target, and which image is then measured or otherwise interpreted by an operator. The currently used but still experimental techniques using conventional ultrasound apparatus produce two dimensional images of the bladder. The diameter of the bladder is then actually measured by the operator off the image on the screen, and the bladder volume is then calculated using that measurement information.

The present invention, however, is substantially different in concept, in that it uses an ultrasound signal to automatically determine selected portions of the border of the bladder, i.e. the location of the front and back walls of the bladder, and using that information, automatically determine the volume of urine in the bladder, rather than to produce a two-dimensional image which is then measured by an operator to determine bladder volume. The inventors utilized the known fact that a returning ultrasound signal from a tissue region of the human body has a relatively high signal level, while the returning signal from a fluid-filled region, such as a bladder, has a very low level, almost zero, because a fluid filled region is anechoic. The returning signal, after processing, provides a clear representation of the selected portions of the border of the bladder, from which the diameter of the bladder is then automatically determined by the processing circuitry. The volume of the bladder is then calculated automatically by the apparatus and the result displayed as a number, instead of a two-dimensional image.

Figures 4, 5:
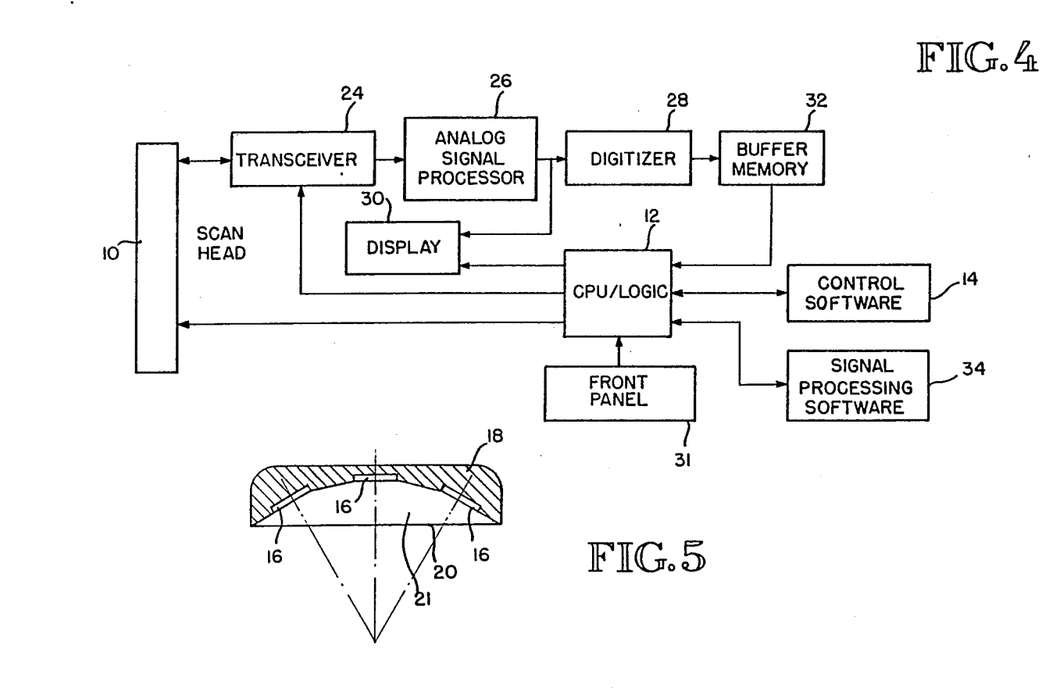
FIG. 4 is a functional block diagram of the apparatus of the present invention.
FIG. 5 is a cross-sectional view showing a linear array embodiment of the transducer portion of the apparatus of FIG. 4.

Referring now to FIG. 4, the apparatus of the present invention includes a scanhead element 10. During use of the invention, the scanhead 10 is placed against the abdomen of the patient and transmits and receives the ultrasound signals. The scanhead 10 includes a transducer which may comprise one or more transducing elements. In one embodiment, the scanhead comprises a single focused transducer which is mounted at the end of a pen-like handle. Such an element is commercially available. In use of the transducer, a transmission gel is applied to the surface of the transducer and it is placed directly on the patient's abdomen.

In another embodiment, a single focused transducer is mounted in a gimbaled structure, which permits freedom of movement along two orthogonal axes. A pair of stepper motors move the transducer through a predetermined path, under computer control. In FIG. 4, microprocessor 12 and the accompanying control software 14 would perform the control function for the stepper motors. The front of the transducer in such an embodiment is covered with a convex neoprene dome, which in use is coated with transmission gel and then placed on the patient's abdomen.

For both of the above scanhead embodiments, it is assumed that the bladder to be measured has a substantially spherical configuration. An ellipsoid configuration is assumed, on the other hand, for a variation of the gimbaled scanhead embodiment mentioned above which includes, as described in more detail below, a single focused transducer mounted in a scanhead for movement through a selected arc in a given plane by means of a stepper motor arrangement.

In still another scanhead embodiment, shown in FIG. 5 and referred to as a sparse linear array, a plurality of focused transducers 16—16 (typically between 5 and 15 in number) are potted on a substrate 18. The individual transducers 16 are mounted at predetermined angles and with predetermined spacing relative to each other such that when the individual transducers are activated in a particular known sequence, accurate volume measurements of any bladder shape are obtained.

In the embodiment of FIG. 5, a flexible neoprene facing sheet 20 forms the front surface of the transducer, with an acoustic fluid 21 filling the region between facing sheet 20 and substrate 18. The transducers 16—16 may also be positioned in a single plane, in which case the transducers are activated sequentially, under computer control, so as to provide coverage over a relatively large region.

Referring to FIG. 4, the transceiver 24 in the present invention is a conventional combined transmitter and receiver, which is switched between its two operational modes at selected times by microprocessor 12. The signal produced by the transceiver in its transmit mode is a typical ultrasound signal, for example 2.25 megahertz pulses in groups or bursts at a pulse repetition frequency of 0.5 kilohertz. The transceiver in the receive mode should have sufficient dynamic range to capture the desired border information In the present case, a dynamic range of 50db will likely be sufficient. The receiver section includes a variable gain amplifier which can be adjusted to compensate for tissue attenuation of the returning signal.

Figure 1:
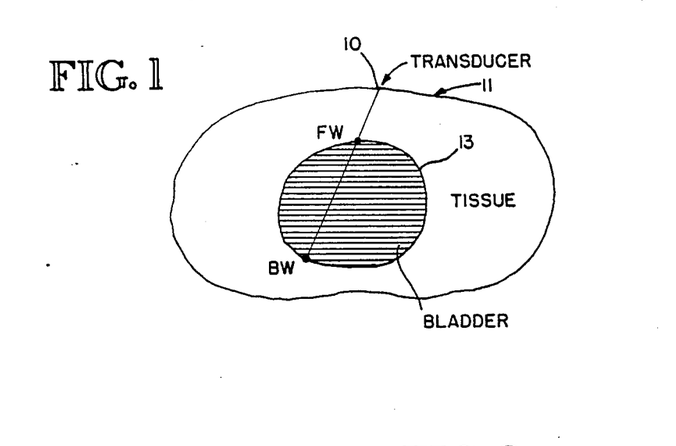
FIG. 1 is a simplified cross-sectional view showing the location of the bladder in human tissue and the relationship thereto of the ultrasound beam.
Figure 2:
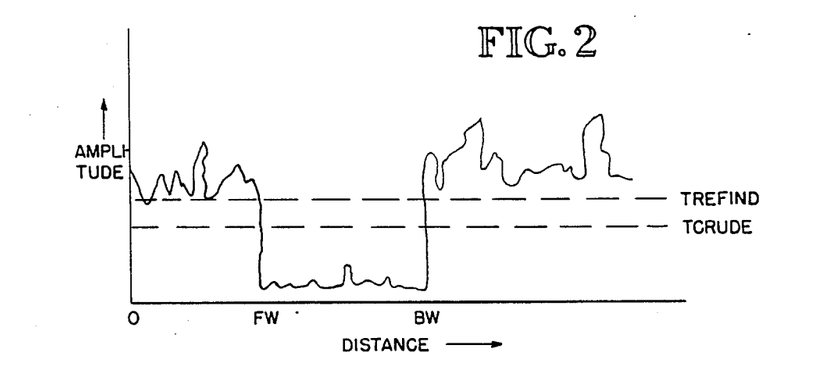
FIG. 2 is a diagram showing the returned ultrasound beam from the patient.

The received signal is applied to an analog signal processor 26, which detects, rectifies and amplifies it. The analog signal processor 26 includes a detector circuit, low and high pass filters and an amplifier. FIG. 2 shows a typical signal output of the analog signal processor. The maximum amplitude of the: signal for the embodiment shown is approximately 2.5 volts. The signal contains information about the borders of the bladder, specified as FW (front wall) and BW (back wall), and the distance therebetween. The remaining portion of the signal is the returning signal from the surrounding tissue.

The output of the analog signal processor is applied to a standard digitizer circuit 28 and a display circuit module 30, such as a liquid crystal display or a CRT. The display of the signal from the analog signal processor is used to give the operator an indication of proper initial positioning of the scanhead on the abdomen of the patient, as will be explained more in detail hereinafter. A switch on the front panel 31 controls whether or not the apparatus is operating in this mode. Digitizer 28 is a conventional analog-to-digital converter which in the embodiment shown comprises two high speed six-bit units in cascade to provide a capability of 12 bits of resolution, although only 7 bits of resolution are actually used in the embodiment shown, i.e. each line of data comprises 256 individual bits of data. It is also possible that the digitizer will include only one six bit unit should such an arrangement provide acceptable results.

The resulting digital signal is stored in a buffer memory 32 and from there is transferred to the microprocessor's main memory. Here the data is operated on by the signal processing software 34. The signal processing software is responsible for the most significant portion of the processing of the received ultrasound signals. The control software 14, on the other hand, is responsible for the timing of the transceiver modes as well as the sequencing of the various functions of the microprocessor and related modules. The control software is conventional, but the signal processing software is unique in concept.

In operation of the apparatus of a first embodiment of the present invention, the scanhead 10 is placed on the abdomen of a patient, with the patient typically being in a supine position. The transducer is moved around on the patient's abdomen until the the visual display is similar to that shown in FIG. 2, which indicates that the transducer is generally over the area of the bladder 13. This is the initial positioning step for the apparatus. The transducer is then rocked gently by the operator about its initial position, so that the ultrasound signals proceed through the bladder, at various angles from this point. The ultrasound signals, which are substantially straight lines, thus are directed through a substantial portion of the cross-sectional area of the bladder 11.

For the first embodiment shown, fifty-seven different individual signal bursts, each referred to as a line of data, are used in order to give an appropriate coverage. However, it should be understood that fewer lines could be used. As the individual lines of data, such as the signal shown in FIG. 2, which is an appropriate analog signal for one line of data, are received by the instrument, each line of data is digitized and individually processed in microprocessor 12 by the signal processing system of the present invention.

The signal processing system comprises a series of key operations which are performed on the data. The first operation is a threshold determination. In this step, the level of noise present in the returning signal is estimated. The overall noise level is first estimated by computing the standard deviation of the entire A-line data. Each A-line corresponds to a single transmission burst. This initial noise estimate is then used as a rough threshold.

A refined noise level estimate is then obtained by calculating the standard deviation for that segment of the signal with amplitudes equal to or below that of the crude threshold. This refined threshold value then represents an estimate of the noise which accompanies the signal returning from the bladder region and is used as the final threshold value for the border detection process.

The next operation is noise cleaning or filtering. Before performing the actual thresholding operation, it is necessary to filter out as much of the noise in the returning signal as possible. However, since the desired border information is associated with large spatial derivatives (and hence relatively high spatial frequencies) a more conventional linear smoothing filter, with low pass characteristics, would remove valuable information. Hence, a non-linear median filter is used. Median filters are characterized by their ability to remove "spikey" noise, while leaving border information intact. In the current embodiment of the invention, the length of the median filter is chosen such that noise spikes with a base of less than 0.5 centimeter in width are removed.

In the next step of thresholding, each element of the filtered signal vector is compared with the refined threshold value established earlier and described above. Each element with original amplitudes which are greater than or equal to the threshold value are set to a preset constant value, while the amplitudes of the other elements are set to zero. Thus, the A-line data is now transformed to a binary signal, with the zero amplitude elements representing the fluid; filled bladder region.

In the next step, the front to back wall separation is estimated. The front wall is determined by locating the first element of the thresholded A-line with an amplitude value of zero. The back wall is determined by locating the first of a set of at least five consecutive non-zero values. The criterion for detecting the actual location of the back wall was developed experimentally to avoid inaccuracies due to reverberation.

Figure 6:
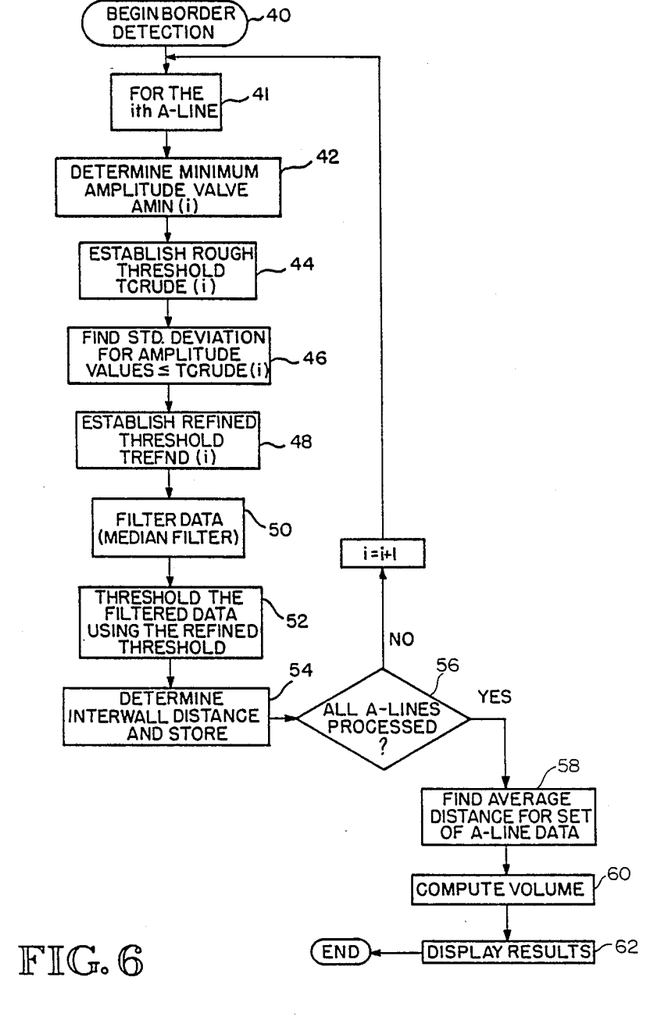
FIG. 6 is a flow chart of the signal processing software portion of the present invention.

A flow chart for the signal processing is shown in FIG. 6. Block 40 represents the beginning or initializing of the border detection process. Block 41 represents the next operation in the process, the selection of the memory bank containing the data set associated with the ith line of data, or more conveniently, the ith A line. The mean value $A_{mean(i)}$ of this data is computed as well as the standard deviation $A_{sdev(i)}$.

In the next operation, represented by block 42, the ith A line is processed to determine a minimum amplitude value $A_{min(i)}$ for the ith line of data. The line of data encompasses the distance from the patient's abdomen to the back wall of the patient's bladder.

In the next operation shown in block 44, a rough threshold value $T_{crude(i)}$ is computed by adding $A_{sdev(i)}$ to $A_{min(i)}$. The rough threshold value $T_{crude(i)}$ is shown in FIG. 2 for that particular signal as an example.

The mean value $B_{mean(i)}$ for all the data points with amplitudes less than $T_{crude(i)}$ is computed and then in the next operation, as shown in block 46, the standard deviation $B_{sdev(i)}$ for this set of data points is computed and the minimum amplitude value $B_{min(i)}$ for all the data points with amplitudes less than $T_{crude(i)}$ is determined. The standard deviation is the square root of the mean of the squares of the differences of the individual data points relative to the mean value $B_{mean(i)}$. As shown in block 48, a refined threshold value Trefnd(i) is then computed by adding $B_{min(i)}$ to $B_{sdev(i)}$. The refined threshold value is also shown in FIG. 2 for that line of data.

The next step, as shown in block 50, is to filter the data, to remove as much noise as possible without harming the signal itself. As discussed above, a conventional low pass filter is not used, since such a filter would remove valuable information from the signal. The median filter, on the other hand, leaves the true signal information, such as the borders in FIG. 2, intact. The operation of a median filter is discussed in detail in a book titled *Digital Imaging Processing* by W. Pratt, which is hereby incorporated by reference. Basically, a three point median filter processes three consecutive bits of data at a time, beginning at the start of a data string. There is thus a filter window of three data elements. For each such group, the value of the middle data point is replaced by the median value of the three data points. The filter window is then moved one data element along the data string, so that substantially each data point in the data string is processed three times by the filter. At the end of the filtering process, the noise spikes have been removed, leaving the border information intact.

Figure 3:
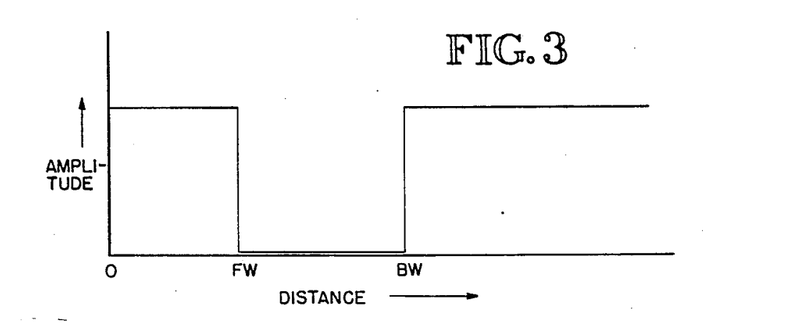
FIG. 3 is a diagram showing the signal of FIG. 2 following processing thereof by the present invention.

In the next operation, shown in block 52, each data point in the A-line data set from the median filter is compared against the refined threshold value $T_{refnd(i)}$. If the amplitude of a particular data point is greater than the threshold value $T_{refnd(i)}$, that data point is set to a predetermined high value, $A_{const}$. If the amplitude f the data point is below the threshold value, the bit is set to zero. The first data point which is below the threshold $T_{refnd(i)}$ (which is hence set to zero) indicates the presence of the front wall of the bladder. There will then be a string of zero data points which represents the bladder region. When there has been five consecutive data points above the threshold, succeeding data points above the threshold are set to a high. The initial high point represents the back wall. The selection of five consecutive high data points as an indication of the back wall is somewhat arbitrary, but is a reliable indication that the back wall has actually been reached. After all the data points in one line (A-line) of data has been processed, the resulting signal is like a binary signal in appearance, with clearly defined borders. FIG. 3 is a processed transformation of the signal of FIG. 2.

The next operation in the processing of the th line of data is shown in block 54. In this step, the interwall distance between the front and back walls of the bladder is computed This distance is stored in a second bank in the microprocessor memory with an associated software pointer to indicate which A-line this distance corresponds to. The above described process is then repeated for the next A-line data, and then further repeated until all of the A-lines have been processed, as indicated by block 56. Following the processing of all of the A-lines, the average of all the A-line distances is calculated, as indicated in block 58, such as by totaling the A-line distances and then dividing by the number of A-lines.

When all of the interwall distance estimates are completed and the average distance has been calculated, the distance information is used with an appropriate geometric model of the bladder and the estimated bladder volume is computed. In one embodiment of the present invention, as pointed out above, a sphere is used as the geometric model of the bladder, i.e. the bladder is assumed to be spherical. Accordingly, the average distance, which is the result of the processing step indicated in block 58, is an accurate representation of the diameter of the bladder, and is used to calculate the volume of the bladder, using the conventional formula, as indicated in block 60. The volume is then displayed as a numerical amount on the front of the apparatus, as indicated in block 62.

Figure 7:
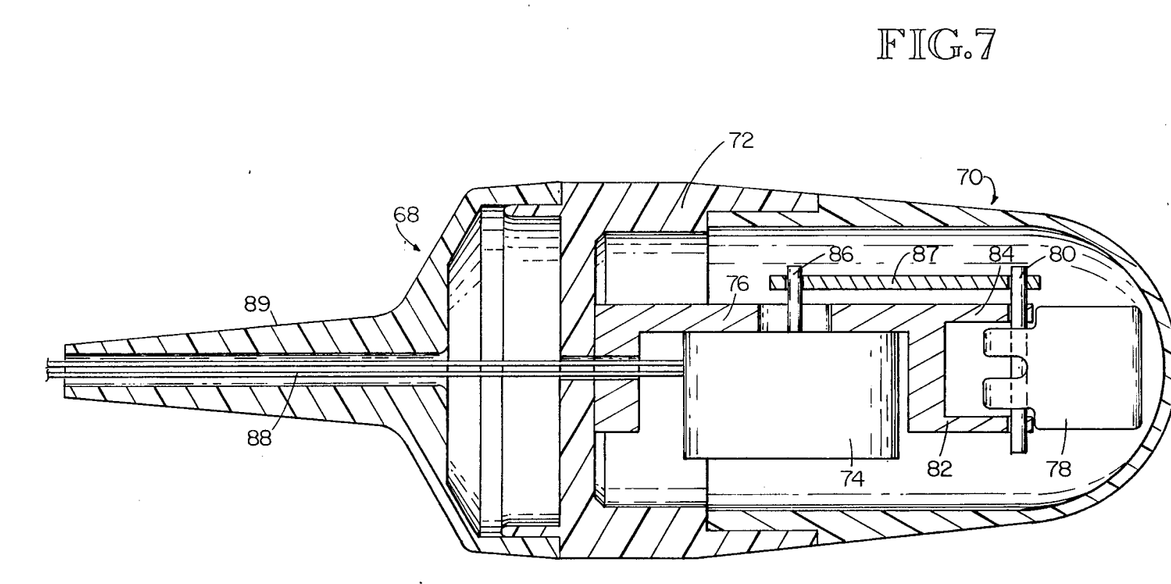
FIG. 7 is a simplified cross-sectional view of another embodiment of the scanhead assembly of the present invention.

Another embodiment uses a scanhead assembly 68 which is mentioned briefly above, and shown in more detail, but still somewhat general form, in FIG. 7. The scanhead 68 includes a body portion 70 which has an internal frame 72. A stepper motor 74 is mounted on a support element 76, which in turn is mounted to the frame 72. A transducer 78 is mounted on a pivot rod 80, which in turn is mounted for rotation on arms 82 and 84 which extend out from support element 76.

The output shaft 86 of stepper motor 74 is connected to pivot rod 80 through a connecting arm 87. Thus, rotation of motor output shaft 86 results in a rotation of pivot rod 80 and hence, the movement of transducer 78 in a plane which extends into the page. Electrical connections to the stepper motor and the transducer are supplied through a cable 88 which extends out through the neck 89 of the scanhead.

The connecting arm 87 is arranged such that each step of the motor 74 will result in a movement of the transducer of approximately 3 degrees. Hence, by stepping the motor 74 thirty-two times, which is typical for the embodiment herein described, but which could be a greater or fewer number, the transducer will move through an arc of 96 degrees. At each step, the transducer is allowed to dampen before it is again pulsed. The returning information from each plate is processed as a single line of data.

Figure 8:
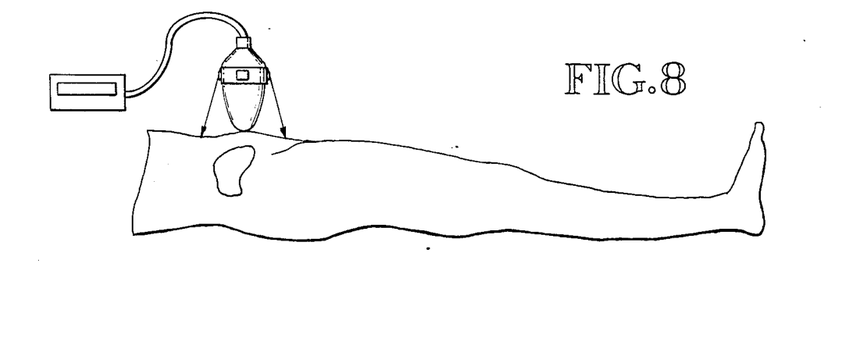
FIG. 8 is an elevational view of a human figure showing the scanhead of FIG. 7 positioned for use in the saggital plane.
Figures 9, 10A, 11:
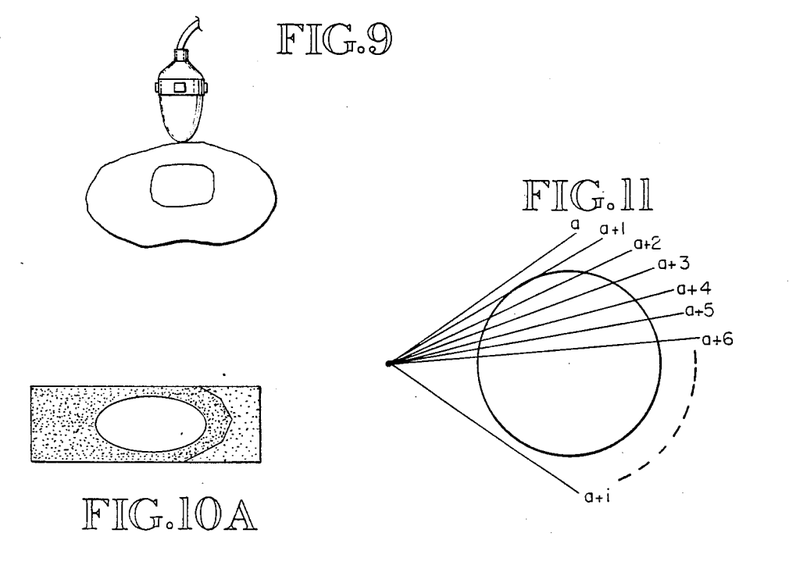
FIG. 9 is a cross-sectional view of a human figure showing the scanhead of FIG. 7 positioned for use in the transverse plane.
FIGS. 10a, 10b and 10c are diagrams showing the visual display on the apparatus during the operation of one embodiment of the present invention.
FIG. 11 is a simplified diagram showing an array of transducer signals relative to a bladder.

Although the above scanhead embodiment can be used in a variety of applications, it is useful in the situation where the geometric model of the bladder is an ellipsoid. In operation, referring to FIG. 8, the operator first observes the plane of movement of the transducer 78 in the scanhead 68 following initiation of the apparatus. The scanhead 68 is then positioned by the operator lightly against the abdomen of the patient such that the plane of the transducer movement is from head to foot, i.e. in the saggital plane. When this is accomplished, an image will appear on the screen such as shown in FIG. 10a. This image is what is known as a binary ultrasound image, and is unprocessed data. The operator moves the scanhead slowly around the area of the abdomen in order to observe the largest diameter image on .the display. When the largest diameter image is displayed, the scanhead is held still. During this time, the transducer continues to move within the scanhead assembly in the saggital plane, by virtue of the action of the stepper motor.

Figure 10B:
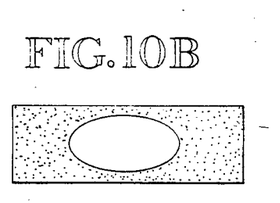
Figure 10C:
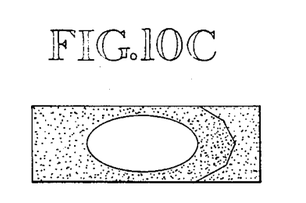

A scan/save switch which is located on either the front panel or the scanhead itself is then activated, so that the actual bladder distance information is stored i.e., there will be stored an A-line data measurement between the back and front borders of the bladder for each position of the transducer as it steps through its arc in the saggital plane. Thus, a succession of distance measurements representing the interior bladder distance from front to back wall is obtained for that first scanhead position, all in the saggital plane. The area of the bladder in that plane is then automatically calculated, using known geometric principles, i.e. by summing successive trapezoids formed by successive A-line distances obtained as indicated above. Since the successive A-lines are separated by a known angle (approximately 3 degrees) the successive trapezoidal areas can be easily calculated and then summed to provide the area calculation. Referring to FIG. 6, block 58 for this embodiment is the area calculation from the successive A lines, instead of the calculation of the average A-line distance. When the area has been calculated, the resulting true cross-sectional image is then displayed, as shown in FIG. 10b. This completes the area calculation in one axis, the saggital plane. The scan/save button is then pushed again, and the unprocessed ultrasound image again appears (FIG. 10c).

The scanhead 68 is then rotated 90 degrees, and the same process as set forth above is carried out, i.e., the scanhead 68 is moved slightly by the operator around the area of the abdomen to locate the spot where the diameter of the bladder is greatest in the orthogonal (transverse) plane. After this position is located, the scanhead 68 is held in that position, the scan/save button is actuated, and another set of A-line data is stored, which is then used to calculate the area of the bladder in the orthogonal plane, as described above. The volume of the ellipsoid is then calculated from the two area calculations, based on known geometric principles. After the calculation is accomplished, the resulting numerical value is then displayed as the bladder volume.

In still another scanhead embodiment which includes an array of transducers, it is possible to compute the volume of irregular bladder shapes, again using conventional geometric computation procedures. The resulting volume measurement is displayed as a numerical amount on the front of the apparatus.

Thus, an apparatus and method has been described and shown which automatically provides an accurate indication of the volume of a bladder, non-invasively, without trauma to the patient, and without intervention by an operator. It is convenient for an operator to use, and initial experimental results have shown the results to have an average difference of 11% compared with catheterization-derived volume measurements.

Although a preferred embodiment of the invention has been disclosed herein for illustration, it should be understood that various changes, modifications and substitutions may be incorporated in such embodiment without departing from the spirit of the invention, as defined by the claims which follow:

We claim:

1. An apparatus for automatically measuring the volume of urine in a human bladder defined by a border, comprising:

means for transmitting a plurality of ultrasound signals into the bladder in first and second planes, wherein the first and second planes are in first and second directions, respectively, which are substantially orthogonal to each other and wherein the transmitting means is movable so that ultrasound signals may be transmitted into the bladder in a plurality of planes in both the first and second directions as the transmitting means is moved;

means for receiving the returning plurality of ultrasound signals from each of said first and second planes;

means for developing initial ultrasound image information of the bladder in said first and second planes;

means for automatically processing the initial ultrasound image information to accurately determine the true border of the bladder in the first and second planes and develop enhanced ultrasound image information therefor;

means for displaying at least one of the initial ultrasound image information and the enhanced ultrasound image information;

means for selectively storing the enhanced ultrasound image information for said first and second planes;

means for automatically determining the distance between the opposing portions of the border of the bladder for each ultrasound signal in said first and second planes from the enhanced ultrasound image information;

means for automatically determining the area of the bladder in said first and second planes from the determined distance information;

means for automatically determining the volume of said bladder and hence the volume of urine in the bladder from the determined areas of the bladder in said first and second planes; and means for displaying said volume in numeral form, wherein the apparatus is characterized in that the initial ultrasound image information, the enhanced ultrasound image information, and the volume of urine in the bladder are provided in substantially real time.

2. An apparatus of claim 1, wherein said area determining means includes means for calculating the area of successive trapezoidal portions of the bladder area in said first and second planes, each trapezoidal portion being defined by two successive ultrasound signals.

3. An apparatus of claim 2, wherein said displaying means includes means for displaying both the initial ultrasound image information and the enhanced ultrasound image information.

4. An apparatus of claim 2, wherein the means for processing includes means for converting the received ultrasound signals, respectively, into a corresponding series of data elements, means for establishing a threshold amplitude value, means for comparing each data element against said threshold value, means for setting the amplitude of each data element to a first value if the data element value is above said threshold value and to a second value if it is below said threshold value, wherein the first value is relatively high compared to the second value, and means for producing a signal comprising a succession of first and second values representative of said series of data elements, further including median filter means for removing noise from the received ultrasound signals.

5. A method for automatically measuring the volume of urine in a human bladder defined by a border, comprising the steps of:

transmitting a plurality of ultrasound signals into the bladder in a first plane in a first direction relative to the bladder;

receiving the returning plurality of ultrasound signals from said first plane in said first direction;

developing initial ultrasound image information of the bladder in said first plane in said first direction;

automatically processing the initial ultrasound image information to determine the actual border of the bladder in said first plane in said first direction and developing enhanced ultrasound image information therefor;

displaying at least one of the initial ultrasound image information and enhanced ultrasound image information;

selectively storing the enhanced ultrasound image information for said first plane in said first direction;

automatically determining the distance between the opposing portions of the border of the bladder in said first plane in said first direction;

automatically determining the area of said bladder in said selected plane in said first direction from said distance information;

repeating the above steps of transmitting, receiving, developing, enhancing, displaying, storing, determining the distance and determining the area of a second plane in a second direction which is substantially orthogonal to said first direction;

automatically determining the volume of said bladder and hence the volume of urine in said bladder from said determined areas of the bladder in said first and second planes; and displaying said bladder volume in numerical form, wherein the method is carried out in substantially real time.

6. A method of claim 5, wherein the first direction is the sagittal direction and the second direction is substantially orthogonal to the sagittal direction.

7. A method of claim 6, wherein said first and second planes encompass, respectively, the largest areas of the bladder in the sagittal direction and the direction orthogonal to the sagittal direction.

8. A method of claim 5, including the step of displaying both the initial ultrasound image information and the enhanced ultrasound image information.

* * * * *

UNITED STATES PATENT AND TRADEMARK OFFICE
CERTIFICATE OF CORRECTION

PATENT NO. : 4,926,871

DATED : May 22, 1990

INVENTOR(S) : Dipankar Ganguly, et al.

It is certified that error appears in the above-identified patent and that said Letters Patent is hereby corrected as shown below:

Claim 4 should be dependent on Claim 1, rather than Claim 2.

Signed and Sealed this

Twenty-third Day of July, 1991

Attest:

HARRY F. MANBECK, JR.

Attesting Officer    Commissioner of Patents and Trademarks